United States Patent [19]  [11] 4,018,792
Winkelmann et al.  [45] Apr. 19, 1977

[54] 5-CYANO-THIOPHEN-2-ALDEHYDE-ISO-THIOSEMICARBAZONES AND PROCESS FOR PREPARING THEM

[75] Inventors: Erhardt Winkelmann; Heinrich Rolly, both of Kelkheim, Taunus, Germany

[73] Assignee: Hoechst Aktiengesellschaft, Frankfurt am Main, Germany

[22] Filed: Feb. 24, 1975

[21] Appl. No.: 552,211

[30] Foreign Application Priority Data

Feb. 26, 1974 Germany .......................... 2409190

[52] U.S. Cl. ................... 260/329 S; 260/329 AM; 260/240 G; 424/275
[51] Int. Cl.² ...................................... C07D 333/00
[58] Field of Search ............... 424/275; 260/329 S, 260/329 AM

[56] References Cited

UNITED STATES PATENTS 3,499,004  3/1970  Winkelmann et al. ............ 260/329

Primary Examiner—Bernard Helfin
Assistant Examiner—A. Siegel
Attorney, Agent, or Firm—Curtis, Morris & Safford

[57] ABSTRACT

Novel 5-cyano-thiophen-2-aldehyde-isothiosemicarbazones are described as well as a process for their manufacture. These compounds are active against viruses and therefore suitable for the prophylaxis and therapy of corresponding infections in humans and animals.

1 Claim, No Drawings

5-CYANO-THIOPHEN-2-ALDEHYDE-ISOTHIOSEMICARBAZONES AND PROCESS FOR PREPARING THEM

It is known from German Patent Application No. 1,543,591 laid open to public inspection that 5-cyano-thiophen-2-aldehyde-thiosemicarbazones are active in vivo against smallpox viruses.

The present invention relates to 5-cyano-thiophen-2-aldehyde-isothiosemicarbazones of the formula I

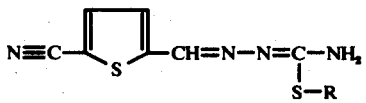

in which R represents saturated or unsaturated, straight or branched alkyl of 1 to 4 carbon atoms or aralkyl, preferably benzyl or phenylethyl, or to a salt thereof with a physiologically tolerable acid.

The invention furthermore relates to a process for preparing the above-specified 5-cyano-thiophen-2-aldehyde-isothiosemicarbazones of the formula I, which comprises
a. reacting a 5-thiophen-2-aldehyde of the formula II

or one of its functional derivatives with an S-alkyl- or S-aralkylisothiosemicarbazide of the formula III

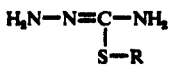

in which R has the meaning given above, or with a salt of such a compound with a physiologically tolerable acid, and optionally setting free from the salt so obtained a compound of the formula I, or
b. reacting a 5-cyano-thiophen-2-aldehyde-thiosemicarbazone of the forumula IV

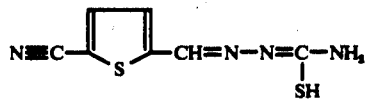

with an alkyl- or aralkyl-halide or -sulfate of the forumula V

Y - R                                                                            (V)

in which R has the meaning given above and Y represents halogen, preferably chlorine, bromine or iodine sulfate, and optionally setting free from the salt so obtained the compound of the formula I.

The starting compound 5-cyanothiophen-2-aldehyde (II) can be obtained according to known methods from 5-halothiophen-2-aldehyde by the reaction with copper-I-cyanide in a polar solvent (c.f. J. org. Chem. 26, 2522, 2525 (1961)).

Instead of the aldehyde, its functional derivatives may be used as starting materials. As such, there may be used, for example, acetals, diacyl compounds, aldehyde-bisulfite compounds, oximes or anilines which can be reacted under the above reaction conditions whith thiosemicarbazide. It is also possible to start from corresponding hydrazones or azines which are reacted with rhodanides. Alkali metal rhodanides such as potassium or sodium rhodanide or ammonium rhodanide are preferably used.

As starting materials of the formula III, there may be used S-methyl-, S-ethyl-, S-n-propyl-, S-isopropyl-, S-n-butyl-, S-isobutyl-, S-allyl-, S-2-methylallyl-, S-propargyl- and S-benzylthiosemicarbazide or a salt thereof, for example a hydrochloride, -bromide, -iodide, a methosulfate or an ethosulfate. These starting substances are obtained by the reaction of thiosemicarbazide with the corresponding alkyl- or aralkyl-halide or alkyl sulfate in a polar solvent such as an alcohol, for example ethanol, propanol or glycol-monoalkyl ether.

As alkyl- or aralkyl-halides or -sulfates, there may be used, for example methyl-, ethyl-, n-propyl-, isopropyl-, n-butyl-, isobutyl-, allyl-, methylallyl-, propargyl- or benzyl-chloride, -bromide, -iodide or -sulfate.

The reactions of a 5-cyano-thiophen-2-aldehyde or of its functional derivatives as described above are carried out in a manner analogous to that of methods described, for example in Houben-Weyl, Methoden der organischen Chemie, 4th Edition, Vol. 9, pages 913 – 915.

a. Thus, for carrying out the process of the invention, it is suitable to allow molar amounts of the components (1 mole of aldehyde and 1 mole of thiosemicarbazide) to react with one another. In general, it is advisable to use a solvent or a dispersing agent. Preferably, the reaction is carried out in a 5 to 20 fold quantity of an organic solvent using in particular low molecular alcohols, for examaple methanol, ethanol, propanol, isopropanol and alkoxyethanols such as methoxy- and ethoxy-ethanol. The reaction of the components in water or mixtures of the above-indicated alcohols with water is also possible.

The reaction temperature may be in the range of from 20° C to 140° C; It is preferred to work at temperatures between 70° and 90° C.

Depending on the temperatures used, the reaction times may range from a few minutes to some hours.

Method a) can be carried out without catalyst. However, the presence of catalytic amounts of an acid may be of advantage for a rapid course of the reaction. As acids, there may be used in this case, for example lower fatty acids such as acetic acid.

The products of the formula I of the invention crystallize in pure form or may be obtained in pure form by recrystallization from a suitable solvent.

The free bases of the formula I are obtained from their salts by reaction with a base or by reaction of the starting substances of the formulae II and III in the presence of a base. The reaction may be carried out in solution or suspension. As bases, there may be used, for example ammonia, trialkyl-amines such as triethylamine, pyridine, picoline, quinoline, alkali metal-, alkaline earth metal-and ammonium-acetates, -carbonates, -bicarbonates, or alkali metal-and alkaline earth metal hydroxides.

According to method b), a 5-cyano-thiophen-2-aldehyde-thiosemicarbazone of the formula IV is reacted with an alkylating agent or aralkylating agent of the formula V. The reaction is suitably carried out in a polar organic solvent, in particular in a low molecular alcohol, for example in one of the alcohols mentioned above for method a). The reaction temperatures may be in the range of from 20° to 140° C; preferably, the reaction is carried at temperatures between 50° and 100° C. Depending on the temperatures used, the reaction times range from a few minutes to some hours. If low boiling alkyl-halides are used, a 20 to 50 % excess over the equimolar quantity is advisable. Upon cooling of the reaction mixture, the salt of the compound of the formula I crystallizes. If necessary, it may be purified by recrystallization as described above.

The novel 5-cyano-thiophen-2-aldehyde-isothiosemicarbozones of the formula I may be used as pharmacologically active agents. They are suitable, in particular, for the prophylaxis and therapy of diseases of humans and animals provoked by viruses and Miyagawanella, for example diseases caused by herpes viruses, trachoma viruses and sheep abortion viruses or by germs causing ornithosis or psittacesis.

The novel compounds may be administered orally, or locally or parenterally. Orally, they are administered in the form of tablets, capsules or sugar-coated coated pills which contain 5 to 500 mg, preferably 50 to 250 mg, of a compound of the formula I in admixture with a pharmaceutically usual carrier and/or excipient. A single dose of the compounds of the invention should be in the range of from 2 to 50 mg per kg of body weight.

Intramuscular or subcutaneous injections are suitable forms of parenteral administration. For local administration, the novel compounds are applied in the form of solutions, ointments, creams or powders.

With animals, the novel compounds are administered orally, as addition to the fodder or drink of the animals. For parenteral administration, intramuscular or subcutaneous injections are suitable. For local administration, they are applied in the form of solutions or powders. A single dose of the compounds of the invention is suitably in the range of from 20 to 1000 mg per kg of body weight of the animal.

The following Examples illustrate the invention.

EXAMPLES 1. 5-Cyano-thiophen-2-aldehyde-S-methyl-isothiosemicarbazonehydro-iodide 13.7 g (0.1 mole) of 5-cyano-thiophen-2-aldehyde were dissolved in 70 ml of ethanol and, after addition of a solution of 22.3 g (0.1 mole) of S-methyl-isothiosemicarbazide-hydroiodide in 70 ml of ethanol, heated for 15 minutes on a steam bath.

The final product precipitated immediately and after it had cooled, it was filtered off with suction and washed with cold ethanol. 28.5 g (corresponding to 79 % of the theoretical yield) of 5-cyano-thiophen-2-aldehyde-S-methyl-isothiosemicarbazone-hydro-iodide in the form of a yellow crystal powder were obtained (melting point 208° C, with decomposition).

By stirring the hydroiodide in aqueous solution or suspension into dilute aqueous ammonia, there was obtained, with an almost quantitative yield, the free base in the form of a yellow powder which after purification by recrystallization from ethanol showed a melting point of 180° C.

The free base was also obtained directly when carrying out the reaction of 5-cyano-thiophen-2-aldehyde with S-methyl-isothiosemicarbazide-hydroiodide in the presence of molar amounts of sodium acetate.

In the same manner, there were obtained with good yields: 2. 5-Cyano-thiophen-2-aldehyde-S-ethyl-isothiosemicarbazonehydroiodide melting at 145° C (free base 94° C) from 5-cyano-thiophen-2-aldehyde and S-ethyl-isothiosemicarbazide-hydroiodide. 3. 5-Cyano-thiophen-2-aldehyde-S-n-propyl-isothiosemicarbazonehydroiodide melting at 174° C (free base 75° C) from 5-cyano-thiophen-2-aldehyde and S-n-propyl-isothiosemicarbazide-hydroiodide. 4. 5-Cyano-thiophen-2-aldehyde-S-allyl-isothiosemicarbazone-hydrobromide melting at 169° C (free base 126° C) from 5-cyano-thiophen-2-aldehyde and S-allyl-isothiosemicarbazide-hydrobromide. 5. 5-Cyano-thiophen-2-aldehyde-S-benzyl-isothiosemicarbazonehydrobromide melting at 208° C (free base 130° C) from 5-cyano-thiophen-2-aldehyde and S-benzyl-isothiosemicarbazide-hydrobromide. 6. The above-mentioned compounds were also obtained by the reaction of 5-cyano-thiophen-2-aldehyde-thiosemicarbazone with the corresponding alkyl- or aralkyl-halides in ethylene-glycol-monomethyl ether at 50°–60° C.

The preparation of 5-cyano-thiophen-2-aldehyde-thiosemicarbozone from 5-cyano-thiophen-2-aldehyde and thiosemicarbazide is described in DOS 1,543,591 (German Patent Application laid open to public inspection). 7. 5-Cyano-thiophen-2-aldehyde-S-propargyl-isothiosemicarbazone-hydrobromide melting at 186° (free base 146° C) was obtained from 5-cyano-thiophen-2-aldehyde and S-propargyl-isothiosemicarbazide hydrobromide.

We claim:

1. 5-cyano-thiophen-2-aldehyde-S-methyl-isothiosemicarbazone, or a salt thereof with a physiologically tolerable acid.

* * * * *